United States Patent [19]

Jadhav

[11] Patent Number: 4,824,657

[45] Date of Patent: Apr. 25, 1989

[54] PROCESS FOR REDUCING SILICON, GERMANIUM AND TIN HALIDES

[75] Inventor: Prabhakar K. Jadhav, Newark, Del.

[73] Assignee: E. I. Du Pont de Nemours and Company, Wilmington, Del.

[21] Appl. No.: 802,230

[22] Filed: Nov. 27, 1985

[51] Int. Cl.$^4$ .................... C01B 6/06; C01B 33/04
[52] U.S. Cl. ................... 423/645; 423/346
[58] Field of Search ................ 423/346, 645

[56] References Cited

U.S. PATENT DOCUMENTS

| | | | |
|---|---|---|---|
| 2,988,427 | 6/1961 | Jenkner | 423/347 |
| 3,043,857 | 7/1962 | Jenkner | 260/429.7 |
| 3,099,672 | 7/1963 | Cooper et al. | 260/448.2 |
| 3,163,590 | 12/1984 | Litz et al. | 423/347 |
| 3,252,752 | 5/1966 | Pohl et al. | 423/347 |
| 3,279,886 | 10/1966 | Nitzsche et al. | 423/347 |
| 3,496,206 | 2/1970 | Berger | 260/448.2 |
| 3,535,092 | 10/1970 | Chalk | 23/366 |
| 3,829,555 | 8/1974 | Muraoka et al. | 423/347 |
| 4,120,937 | 10/1978 | Blount | 123/347 |
| 4,295,986 | 10/1981 | Gordon | 252/188 |

FOREIGN PATENT DOCUMENTS

| | | | |
|---|---|---|---|
| 0052808 | 6/1982 | European Pat. Off. | 423/347 |
| 0149363 | 7/1985 | European Pat. Off. | 423/645 |
| 909950 | 11/1962 | United Kingdom . | |

*Primary Examiner*—John Doll
*Assistant Examiner*—Robert M. Kunemund

[57] ABSTRACT

A process for reducing halogen-containing compounds of silicon, germanium or tin with lithium hydride in the presence of tetrahydrofuran wherein the lithium hydride is first heated in the tetrahydrofuran and then the halogen-containing compound is added.

12 Claims, No Drawings

PROCESS FOR REDUCING SILICON, GERMANIUM AND TIN HALIDES

TECHNICAL FIELD

This invention relates to a process for reducing halides or organo halides of silicon, germanium and tin with lithium hydride in the presence of tetrhydrofuran to produce the corresponding hydrides.

BACKGROUND AND SUMMARY OF INVENTION

Hydrides of silicon, germanium and tin are commercially valuable compounds that have been long known, but difficult to make. Hydrides of silicon, for example, may be hydrolized in aqueous acidic solutions to form siloxanes which are useful in waterproofing fabrics.

In the past, these hydrides of silicon, germanium and tin have been prepared by a number of reduction processes which are exemplified in the patents discussed in the following paragraphs. Each of the processes has deficiencies which are overcome by the instant process.

U.S. Pat. No. 4,295,986 to Gordon teaches the reduction of silicon, germanium and tin halides using an alkali metal hydride catalytically activated by a solution of an alkali borohydride in a suitable polyether solvent. Care must be exercised to avoid depletion of the alkali metal hydride since, if it is consumed, reduction will continue with the alkali borohydride in solution causing borane to build up in concentration finally liberating spontaneously flammable diborane gas and/or causing undesirable rearrangements of some reduction products.

U.S Pat. No. 3,099 672 to Cooper et al. teaches a process for the reduction of organo halogen silanes, organo alkoxy silanes, and silicon tetrachloride with sodium hydride at temperatures of from 175° to 350° C. This process is restricted to cases where reactants and products are stable at the high temperatures required. It also involves excessive energy consumption, thus raising the cost of making silicon hydrides. Moreover, with the higher temperatures, additional problems of control and the presence of undesirable by-products are injected into the process.

U.S. Pat. No. 3,535,092 to Chalk teaches a process that can be run at lower temperatures than the Cooper et al. process. Chalk teaches a reduction of halogen-contining silicon compounds with sodium hydride in the presence of an aprotic solvent selected from the class hexaalkylphosphoramides, octaalkylpyrophosphoramides, tetraalkylureas, and mixtures thereof. This class of solvents is expensive and suspected to be carcinogenic.

U.S. Pat. No. 3,043,857 to Jenkner teaches reduction of halides of silicon, germanium and tin with alkali metal hydride in the presence of metal organic compounds of boron, gallium, and aluminum at 40° to 180° C. in an inert organic solvent. Many of the catalysts of this process are pyrophoric, thus posing a fire risk. Also, separation of the product can be extremely difficult due to the close boiling points of the product and some of the metal organic compounds of boron, gallium and aluminum that are used. Jenkner also mentions the non-pyrophoric alkoxy and phenoxy compounds of boron and aluminum as catalysts, but these are much less active than the pyrophoric alkyls and require high temperatures and concentrations to be effective.

U.S Pat. No. 3,496,206 to Berger teaches reduction of organo silicon halide with alkali metal hydride in the presence of alkyl aluminum halide at temperatures of −20° to 150° C. in a substantially inert organic solvent. This process is similar to that of Jenkner but uses a less volatile catalyst form.

The process of the instant invention comprises reacting halogen compounds of silicon, germanium and tin with lithium hydride in the presence of tetrahydrofuran (THF) as a solvent at temperatures between 25° C. and 67° C. Where the reduction products have a boiling point less than that of THF, stoichiometric amounts of lithium hydride can be used. For products with boiling points greater than that of THF, an excess of lithium hydride is required. Likewise, the volumetric efficiency of the reaction is affected by the boiling point of the desired product. Where the boiling point is less than that of THF, the volumetric efficiency is excellent, that is, about 0.6 to 1.7 moles of THF per mole of the starting organohalo compound is required. Where the boiling point of the desired product is greater than that of THF, an eight to ten fold excess of THF is required. This probably is the result of the product which is a liquid at reaction conditions accumulating in the reaction vessel as the reaction progresses and affecting the overall polarity of the mixture. Where the product has a lower boiling point than THF, it is a gas under reaction conditions and distills out of the reaction vessel.

This process has several advantages over the processes reported in the art. The solvent is a less-expensive, noncarcinogenic solvent; the safety hazards associated with using pyrophoric materials are avoided; it is not critical to maintain an excess of the alkali hydride; and high temperatures are avoided. The process also has high yields, is not restricted by long reaction times, can be run batchwise or continuously, and yields a product that is easily separated from the reaction mixture.

DETAILED DESCRIPTION OF THE INVENTION

The present invention relates to the reduction of halogen-containing silicon, germanium and tin compounds. The halides of this invention include compounds containing from one to four halogens bonded to the silicon, germanium, or tin. Any remaining valences are satisfied by members selected from the class consisting of hydrogen and hydrocarbon radicals such as alkyl radicals, alkenyl radicals, aryl radicals and aralkyl radicals. The preferred halo moiety is chlorine and the preferred organo moiety is either the ethyl or methyl radical.

The solvent used in the reaction is tetrahydrofuran (THF), present in at least about 0.5 moles per mole of halide. Preferably, when the boiling point of the resulting product is less than that of THF, the THF should be present in a mole ratio of 0.5 to 2:1 of halide. The most preferred mole ratio in that case is 1.5:1. Where the resulting product will have a boiling point greater than that of THF, excess THF is required. In that case, the preferable mole ratio should be 4 to 20:1 of halide present.

The reducing agent of this invention is lithium hydride, present in at least one mole per mole of halide. Where the resulting product has boiling point greater than that of the THF, the lithium hydride preferably should be greater than two moles per mole of halide.

The reaction should be run at 25° to 67° C. and preferably at the refluxing temperature of THF. The reaction preferably should be carried out in an inert atmosphere. Operating pressure is not critical.

The order and method of addition have been found to be critical. The lithium hydride and THF must first be added to the reaction vessel. The lithium hydride and THF must then be heated. The halide may then be added to the reaction mixture. Preferably the halide should be added slowly.

The invention is illustrated but not limited by the following examples. All operations were carried out in oven-dried glassware and under nitrogen atmosphere.

EXAMPLE 1

Reduction of Chlorotrimethylsilane

A 250-ml R.B. flask equipped with septum inlet, magnetic stirring bar and reflux condenser was charged with 4.0 g (0.5 mole) of lithium hydride and 60 ml of tetrahydrofuran (THF). The reaction mixture was heated (oil bath temperature was 85° C.) to maintain a continuous reflux of THF (boiling point 67° C.). Then, 63.5 ml (0.5 mole) of chlorotrimethylsilane was added through septum inlet at 0.4 ml/minutes using a syringe pump. Trimethylsilane (b.p. 7° C.) formed, was allowed to pass through a glass trap cooled at −78° C. (dry ice-acetone bath). After the addition was complete, the reaction mixture was flushed with nitrogen through septum inlet for 15–30 minutes to displace trimethylsilane. The product was distilled (b.p. 7° C.) to provide 35.9 g (97% yield) of trimethylsilane.

EXAMPLE 2

Reduction of Chlorodimethylsilane

A 250-ml R.B. flask equipped with septum inlet, magnetic stirring bar and reflux condenser was charged with 4.0 g (0.5 mole) of lithium hydride and 60 ml of THF. The reaction mixture was heated as in Example 1 to maintain a continuous reflux of THF and 54.5 ml chlorodimethylsilane (0.5 mole) was added at 0.4 ml/minute. The generated dimethylsilane (b.p. −20° C.) was condensed in a glass trap cooled at −78° C. (dry ice-acetone bath). After the addition was complete, the reaction mixture was flushed with nitrogen as in Example 1. The product was distilled to provide 26.3 g (88% yield) of dimethylsilane.

EXAMPLE 3

Reduction of Dichlorodimethylsilane

A 250-ml R.B. flask equipped with septum inlet, magnetic stirring bar and reflux condenser was charged with 8.0 g (1.0 mole) of lithium hydride and 120 ml of THF. As in Example 1, the reaction mixture was heated to reflux and 60.6 ml dichlorodimethylsilane (0.5 mole), was slowly added (0.4 ml/minute). The generated dimethylsilane (b.p. −20° C.) was condensed in a glass trap and, after the addition was complete, nitrogen was bubbled through the reaction mixture. The product was distilled to provide 27.0 g (90% yield) of dimethylsilane.

EXAMPLE 4

Reduction of Dichloromethylsilane

A 250-ml R.B. flask equipped with septum inlet, magnetic stirring bar and reflux condenser was charged with 8.0 g (1.0 mole) of lithium hydride and 120 ml of THF. As in Example 1, the reaction mixture was heated to reflux and 52.0 ml dichloromethylsilane (0.5 mole) was slowly added (0.4 ml/minute). The generated methylsilane (b.p. −57° C.) was condensed in a glass trap and, after the addition was complete, nitrogen was bubbled through the reaction mixture. The product was distilled to provide 19.82 g (86% yield) of methylsilane.

EXAMPLE 5

Reduction of Chlorotriethylsilane

A 100-ml R.B. flask fitted with septum inlet, reflux condenser and magnetic stirrer was charged with 0.8 g (0.1 mole) of lithium hydride and 50 ml THF. The contents were stirred and heated to reflux. Then 8.4 ml (0.05 mole) chlorotriethylsilane was then added at a rate of 0.2 ml/minute. After the addition was complete, the mixture was further refluxed for seven (7) hours. The progress of the reaction was monitored by gas chromatographic analysis of aliquots periodically taken. The reaction was found to complete at the end of seven hours. The contents were cooled, filtered, and fractionated to separate the product triethylsilane (b.p. 107°–108° C.) from THF. The product was distilled to produce 4.76 g (82% yield) triethylsilane.

While the examples have been limited to silicon compounds containing chlorine as the reducible electronegative function, germanium or tin compounds containing other electronegative functions from the halogen family can be reduced with modifications within the scope of this invention.

I claim:

1. A process for making hydrides of silicon, germanium or tin which consisting essentially of reacting lithium hydride in tetrahydrofuran with halogen-containing compounds of silicon, germanium or tin, said process comprising the following steps:
    (1) Adding at least one mole of lithium hydride to at least 0.5 mole tetrahydrofuran per mole of the halogen-containing compound and heating; then
    (2) Adding the halogen-containing compound.

2. the process of claim 1 wherein the halogen-containing compound contains from one to four halogens bonded to the silicon, germanium or tin and has any remaining valences satisfied by hydrogen or alkyl, alkenyl, aryl or aralkyl radicals.

3. The process of claim 2, wherein the halogen is chlorine.

4. The process of claim 3 wherein the remaining valences are satisfied by hydrogen or methyl or ethyl radicals.

5. The process of claim 3, wherein the halogen-containing compound is a halogen-containing compound of silicon.

6. The process of claim 3 wherein the halogen-containing compound is chlorotrimethylsilane, chlorodimethylsilane, dichlorodimethylsilane, dichloromethylsilane or chlorotriethylsilane.

7. The process of claim 1 wherein the hydride has a boiling point less than the boiling point of tetrahydrofuran.

8. The process of claim 7 wherein the mole ratio of tetrahydrofuran to halogen-containing compound is from about 0.5:1 to 2:1.

9. The process of claim 7 wherein the mole ratio is about 1.5:1.

10. The process of claim 1 wherein the hydride has a boiling point greater than that of tetrahydrofuran.

11. The process of claim 10 wherein the mole ratio of tetrahydrofuran to halogen-containing compound is from about 4:1 to 20:1 and the mole ratio of lithium hydride to the halogen-containing compound is at least 2:1.

12. The process of claim 1 wherein the lithium hydride and tetrahydrofuran are heated to reflux.

* * * * *